US008743195B2

(12) United States Patent
Najmabadi et al.

(10) Patent No.: US 8,743,195 B2
(45) Date of Patent: Jun. 3, 2014

(54) WHOLE SLIDE FLUORESCENCE SCANNER

(75) Inventors: Peyman Najmabadi, Vista, CA (US);
Gregory J. Crandall, Vista, CA (US);
Aaron Alan Stearrett, Vista, CA (US);
Dirk G. Soenksen, Vista, CA (US);
Christopher Adam Lee, Vista, CA
(US); Cynthia Perz, Vista, CA (US)

(73) Assignee: Leica Biosystems Imaging, Inc., Vista, CA (US)

( * ) Notice: Subject to any disclaimer, the term of this patent is extended or adjusted under 35 U.S.C. 154(b) by 463 days.

(21) Appl. No.: 12/990,576

(22) PCT Filed: Oct. 23, 2009

(86) PCT No.: PCT/US2009/061957
§ 371 (c)(1),
(2), (4) Date: Nov. 1, 2010

(87) PCT Pub. No.: WO2010/048584
PCT Pub. Date: Apr. 29, 2010

(65) Prior Publication Data
US 2011/0115897 A1 May 19, 2011

Related U.S. Application Data

(60) Provisional application No. 61/108,431, filed on Oct. 24, 2008.

(51) Int. Cl.
*G01N 21/64* (2006.01)
*G02B 21/00* (2006.01)
*G02B 21/16* (2006.01)

(52) U.S. Cl.
CPC .............. *G01N 21/64* (2013.01); *G02B 21/00* (2013.01); *G02B 21/16* (2013.01)
USPC .............................. 348/79; 382/133; 382/128

(58) Field of Classification Search
CPC ..... G01N 21/6458; G02B 21/00; G02B 21/16
See application file for complete search history.

(56) References Cited

U.S. PATENT DOCUMENTS

| 3,643,015 A | 2/1972 | Davidovits et al. |
| 4,672,559 A | 6/1987 | Jansson |

(Continued)

FOREIGN PATENT DOCUMENTS

| CA | 2229175 | 8/1999 |
| DE | 2340860 | 3/1974 |

(Continued)

OTHER PUBLICATIONS

PCT/ISA/237, PCT/US2009/061957, Written Opinion, Korean Intellectual Property Office, May 18, 2010.

(Continued)

*Primary Examiner* — Jayanti K Patel
*Assistant Examiner* — Reza Aghevli
(74) *Attorney, Agent, or Firm* — Pattric J. Rawlins; Procopio, Cory, Hargreaves & Savitch LLP

(57) ABSTRACT

A whole slide fluorescence digital pathology system is provided that uses a monochrome TDI line scan camera, which is particularly useful in fluorescence scanning where the signal is typically much weaker than in brightfield microscopy. The system uses oblique brightfield illumination for fast and accurate tissue finding and employs a unique double sweep focus scoring and objective lens height averaging technique to identify focus points and create a focus map that can be followed during subsequent scanning to provide autofocusing capability. The system also scans and analyzes image data to determine the optimal line rate for the TDI line scan camera to use during subsequent scanning of the digital slide image and it also creates a light profile to compensate for loss of illumination light due to roll off.

8 Claims, 4 Drawing Sheets

(56) References Cited

U.S. PATENT DOCUMENTS

| | | | |
|---|---|---|---|
| 4,673,988 A | 6/1987 | Jansson et al. | |
| 4,700,298 A | 10/1987 | Palcic et al. | |
| 4,742,558 A | 5/1988 | Ishibashi et al. | |
| 4,744,642 A | 5/1988 | Yoshinaga et al. | |
| 4,760,385 A | 7/1988 | Jansson et al. | |
| 4,777,525 A | 10/1988 | Preston et al. | |
| 4,806,015 A | 2/1989 | Cottingham | |
| 4,845,552 A | 7/1989 | Jaggi et al. | |
| 4,926,489 A | 5/1990 | Danielson | |
| 4,960,999 A | 10/1990 | McKean et al. | |
| 4,987,480 A | 1/1991 | Lippman et al. | |
| 5,086,477 A | 2/1992 | Yu et al. | |
| 5,172,228 A | 12/1992 | Israelsen | |
| 5,185,638 A | 2/1993 | Conzola | |
| 5,187,754 A | 2/1993 | Currin et al. | |
| 5,231,663 A | 7/1993 | Earl et al. | |
| 5,400,145 A | 3/1995 | Suita et al. | |
| 5,412,214 A | 5/1995 | Suzuki et al. | |
| 5,416,609 A | 5/1995 | Matsuda | |
| 5,434,629 A | 7/1995 | Pearson et al. | |
| 5,489,772 A * | 2/1996 | Webb et al. | 250/208.1 |
| 5,495,535 A | 2/1996 | Smilansky et al. | |
| 5,578,832 A | 11/1996 | Trulson et al. | |
| 5,633,948 A | 5/1997 | Kegelmeyer, Jr. | |
| 5,644,356 A | 7/1997 | Swinson et al. | |
| 5,649,022 A | 7/1997 | Maeda et al. | |
| 5,650,813 A | 7/1997 | Giblom et al. | |
| 5,672,861 A | 9/1997 | Fairley et al. | |
| 5,710,835 A | 1/1998 | Bradley | |
| 5,714,756 A | 2/1998 | Park et al. | |
| 5,754,291 A | 5/1998 | Kain | |
| 5,784,162 A | 7/1998 | Cabib et al. | |
| 5,790,710 A | 8/1998 | Price et al. | |
| 5,793,969 A | 8/1998 | Kamentsky et al. | |
| 5,796,861 A | 8/1998 | Vogt | |
| 5,822,055 A | 10/1998 | Tsai et al. | |
| 5,834,758 A | 11/1998 | Trulson et al. | |
| 5,845,013 A | 12/1998 | Bouchard et al. | |
| 5,872,591 A | 2/1999 | Truc et al. | |
| 5,895,915 A | 4/1999 | Deweerd | |
| 5,912,699 A | 6/1999 | Hayenga et al. | |
| 5,922,282 A | 7/1999 | Ledley | |
| 5,932,872 A | 8/1999 | Price | |
| 5,943,122 A | 8/1999 | Holmes | |
| 5,963,314 A | 10/1999 | Worster et al. | |
| 5,968,731 A | 10/1999 | Layne et al. | |
| 5,991,444 A | 11/1999 | Burt et al. | |
| 5,999,662 A | 12/1999 | Burt et al. | |
| 6,002,789 A | 12/1999 | Olsztyn et al. | |
| 6,005,964 A | 12/1999 | Reid et al. | |
| 6,049,421 A | 4/2000 | Raz et al. | |
| 6,078,681 A | 6/2000 | Silver | |
| 6,091,846 A | 7/2000 | Lin et al. | |
| 6,101,265 A | 8/2000 | Bacus et al. | |
| 6,211,955 B1 | 4/2001 | Basiji et al. | |
| 6,215,892 B1 | 4/2001 | Douglass et al. | |
| 6,262,838 B1 | 7/2001 | Montagu | |
| 6,272,235 B1 | 8/2001 | Bacus et al. | |
| 6,288,782 B1 | 9/2001 | Worster et al. | |
| 6,316,774 B1 * | 11/2001 | Giebeler et al. | 250/458.1 |
| 6,327,377 B1 | 12/2001 | Rutenberg et al. | |
| 6,330,348 B1 | 12/2001 | Kerschmann et al. | |
| 6,438,268 B1 | 8/2002 | Cockshott et al. | |
| 6,519,357 B2 | 2/2003 | Takeuchi | |
| 6,580,502 B1 | 6/2003 | Kuwabara | |
| 6,594,401 B1 | 7/2003 | Metcalfe et al. | |
| 6,711,283 B1 | 3/2004 | Soenksen | |
| 6,714,281 B1 | 3/2004 | Amano et al. | |
| 6,763,140 B1 | 7/2004 | Skoll | |
| 6,917,696 B2 | 7/2005 | Soenksen | |
| 7,035,478 B2 | 4/2006 | Crandall et al. | |
| 7,106,895 B1 | 9/2006 | Goldberg et al. | |
| 7,155,049 B2 | 12/2006 | Wetzel et al. | |
| 7,212,667 B1 | 5/2007 | Shin et al | |
| 7,247,825 B2 | 7/2007 | Soenksen et al. | |
| 7,312,919 B2 | 12/2007 | Overbeck | |
| 7,338,168 B2 | 3/2008 | Cartlidge et al. | |
| 7,428,324 B2 | 9/2008 | Crandall et al. | |
| 7,457,446 B2 | 11/2008 | Soenksen | |
| 7,518,652 B2 * | 4/2009 | Olson et al. | 348/351 |
| 7,826,649 B2 | 11/2010 | Crandall et al. | |
| 2001/0012069 A1 | 8/2001 | Derndinger et al. | |
| 2001/0017941 A1 | 8/2001 | Chaddha | |
| 2003/0036855 A1 * | 2/2003 | Harris et al. | 702/19 |
| 2003/0048933 A1 * | 3/2003 | Brown et al. | 382/128 |
| 2004/0170312 A1 * | 9/2004 | Soenksen | 382/133 |
| 2004/0256538 A1 | 12/2004 | Olson et al. | |
| 2006/0147901 A1 * | 7/2006 | Jan et al. | 435/4 |
| 2006/0209309 A1 | 9/2006 | Feng | |
| 2006/0247862 A1 * | 11/2006 | Arini et al. | 702/19 |
| 2007/0160270 A1 * | 7/2007 | Arini et al. | 382/128 |
| 2009/0028414 A1 | 1/2009 | Crandall et al. | |
| 2011/0221882 A1 * | 9/2011 | Crandall et al. | 348/79 |

FOREIGN PATENT DOCUMENTS

| | | |
|---|---|---|
| DE | 10232242 | 2/2004 |
| EP | 0339582 | 4/1989 |
| EP | 0363931 | 4/1990 |
| EP | 0796005 | 9/1997 |
| EP | 0871052 | 10/1998 |
| JP | 4194905 | 7/1992 |
| JP | 0576005 | 3/1993 |
| JP | 9197290 | 7/1997 |
| JP | 11211988 | 8/1999 |
| JP | 2001210263 | 8/2001 |
| JP | 2002042706 | 2/2002 |
| JP | 07243823 | 4/2009 |
| WO | WO9114342 | 9/1991 |
| WO | WO9720198 | 6/1997 |
| WO | WO9820445 | 5/1998 |
| WO | WO9839728 | 9/1998 |
| WO | WO9844333 | 10/1998 |
| WO | WO9844446 | 10/1998 |
| WO | WO9852018 | 11/1998 |
| WO | WO0184209 | 11/2001 |

OTHER PUBLICATIONS

PCT/ISA/210, PCT/US2009/061957, International Search Report, Korean Intellectual Property Office, May 18, 2010.

Adobe Developers Association, "TIFF" revision 6.0, Jun. 3, 1992; Adobe Systems Incorporated, Mountain View, CA, 121 pages.

Cited reference analyses, obtained from U.S. Patent Office Website from U.S. Appl. No. 95/000,518, dated Nov. 23, 2009, 41 pages.

European Patent Office Supplementary search report, European Patent Application No. 04750306.5-2217, issued Sep. 11, 2008, 4 pages.

Hamilton, Eric, JPEG File Interchange Format:, Version 1.02, Sep. 1, 1992; C-Cube Microsystem, Milpitas, CA, 9 pages.

Hunt, Circumference imaging for optical based identification of cylindrical and conical objects, Feb. 1, 1997, 13 pages.

International Search Report and Written Opinion for PCT/US2009/061957 issued May 18, 2010, 12 pages.

PCT/IPEA/409 International Application No. PCT/US04/11966, International Preliminary Examination Report, Apr. 22, 2005.

PCT/ISA/210 International Application No. PCT/US04/11966, International Search Report issued Oct. 13, 2004, 1 page.

PCT/ISA/237 International Application No. PCT/US04/11966, Written Opinion of the International Searching Authority issued Oct. 13, 2004, 16 pages.

Sluder, Greenfield and WOLD, David E. editors, Methods in Cell Biology, vol. 56, Chapter 2, 1998, ISBN 879-0-12-564158-6, 334 pages.

* cited by examiner

WHOLE SLIDE FLUORESCENCE SCANNER

RELATED APPLICATION

The present application is the U.S. national stage application of international application number PCT/US09/61957 filed 23 Oct. 2009 and claims priority to U.S. provisional patent application Ser. No. 61/108,431 filed 24 Oct. 2008, each of which is incorporated herein by reference in its entirety.

BACKGROUND

1. Field of the Invention

The present invention is generally related to digital pathology using line scan cameras and more particularly related to scanning fluorescent microscope samples using a line scan camera.

2. Related Art

Brightfield scanners rely on the use of sensitive color cameras such as line scan cameras or area scan cameras. Line scan cameras, which are superior to area scan cameras for digital pathology, require precise movement of the slide (and the stage upon which the slide rests) in synchronization with the data capture parameters of the camera.

The significant advantages of line scan cameras in brightfield scanning have yet to be successfully adopted with fluorescence scanners because the inherent differences between fluorescence and brightfield samples requires new techniques for automated scan and display of fluorescence samples. One fundamental difference between brightfield and fluorescence scanning is that fluorescence scanning typically uses light that is reflected off of the sample (e.g., epi-illumination) while brightfield scanning uses light that is transmitted through the sample.

In fluorescence scanning, fluorescence molecules (also called fluorochromes) are photon sensitive molecules that can absorb light at a specific wavelength (excitation) and emit light at a higher wavelength (emission). As the efficiency of this photoluminescence phenomenon is very low, the amount of emitted light is also very low. Because of the weaker signals in fluorescence scanning, a single array line scan camera typically used with brightfield scanning would be suboptimal because it would need to operate at a lower line scanning rate in order to create a high fidelity image.

Additionally, the task of finding the tissue of fluorescence samples is extremely challenging because the samples are typically transparent in brightfield illumination, which is the most efficient illumination mode in which to do tissue finding. Even more challenging with fluorescence scanning using a line scan camera is the task of automatic focus plane recognition. Another significant challenge with fluorescence scanning is determining the optimal exposure time for fluorescent samples because they vary significantly in emission intensity. Other very significant challenges related to fluorescence scanning using a line scan camera include the scanning workflow required for tissue finding, autofocus, autoexposure, multi-channel scanning (scanning samples having multiple fluorochromes with different emission wavelengths), stripe alignment, and illumination (e.g., epi-illumination). Additionally, with respect to multi-channel images, new and significant challenges are present for data management, visualization, and analysis related to the resulting image data.

Therefore, what is needed is a system and method that allows for the use of a line scan camera in fluorescence scanning and overcomes the significant problems found in conventional systems as described above.

SUMMARY

Accordingly, to provide the speed and accuracy advantages of a line scan camera system in fluorescence scanning, a fluorescence digital pathology system is provided that uses a monochrome time delay integration ("TDI") line scan camera having multiple linear arrays ("TDI line scan camera"). The monochrome TDI line scan camera enables higher line rates for scanning fluorescence samples by using multiple linear arrays that provide increased sensitivity compared to a single array line scan camera. This is particularly useful in fluorescence scanning where the signal is typically much weaker than in brightfield microscopy. The system also uses oblique brightfield illumination for fast and accurate tissue finding and employs a unique double sweep focus scoring and objective lens height averaging technique to identify focus points and create a focus map that can be followed during subsequent scanning to provide autofocusing capability.

The system additionally uses the histogram of a small scanned area of the sample to determine the optimal line rate for the TDI line scan camera during scanning and thereby provides optimal exposure time for scanning the fluorescence sample. The system also employs an efficient scanning workflow to scan the multiple channels of a fluorescence sample. With respect to stripe alignment, the system uses contrast in the overlap region between adjacent stripes to align adjacent stripes when sufficient contrast is available and also aligns adjacent stripes for each channel in a multi-channel sample. Moreover, the digital pathology system has an illumination system that optionally employs beam shaping to illuminate an oval or rectangular area that is in close registration with the rectangular sensor of the TDI line scan camera, which preserves the fluorescence sample and also allows for shorter exposure times. The system also provides data management capabilities to address the challenges associated with scans of multi-channel samples. The system similarly provides visualization and analysis capabilities to address single and multi-channel viewing and analysis of the digital slide image.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Embodiments disclosed herein provide for a whole slide fluorescence scanning system and methods of operation of a fluorescence scanning system. After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
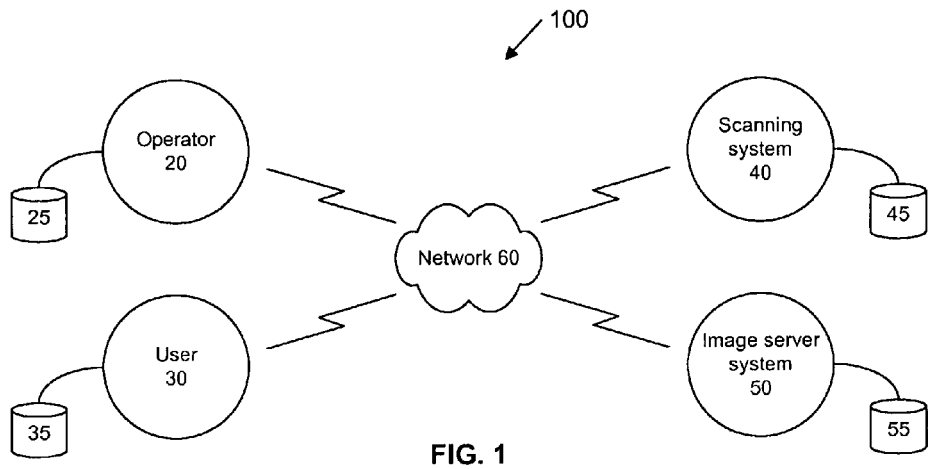
FIG. 1 is a network diagram illustrating an example fluorescence scanner system according to an embodiment of the invention.

FIG. 1 is a network diagram illustrating an example fluorescence scanner system 100 according to an embodiment of the invention. In the illustrated embodiment, the system 100 comprises a fluorescence scanning system 40 that is configured with a data storage area 45. The fluorescence scanning system 40 is communicatively coupled with an operator station 20, a user station 30, and an image server system 50 via a data communication network 60. Each of the operator station 20, user station 30, and image server system 50 are configured with a data storage area 25, 35 and 55, respectively. The data storage areas 25, 35, 45 and 55 may include volatile and persistent storage including for example, random access memory and hard disk drives. The network 60 can be any of a variety of network types including wired and wireless, public and private, or any combination of communication networks such as the Internet.

In operation, the fluorescence scanning system 40 digitizes a plurality of fluorescence samples to create a corresponding plurality of digital slide images that can be stored on the fluorescence scanning system 40 or on the image server system 50. The fluorescence scanning system 40 may be operated directly or remotely by an operator at the operator station 20. The fluorescence digital slide images located at the fluorescence scanning system 40 or the image server system 50 may be viewed by a user at the user station 30, where the digital image data is provided to the user station 30 via the network 60.

Figure 2:
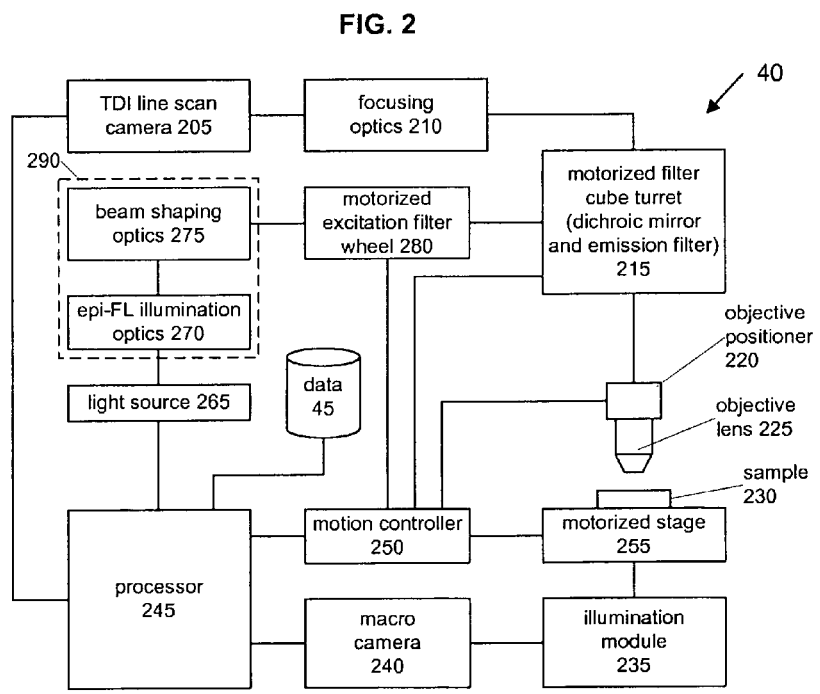
FIG. 2 is a block diagram illustrating an example fluorescence scanner system according to an embodiment of the invention.

FIG. 2 is a block diagram illustrating an example fluorescence scanner system 40 according to an embodiment of the invention. In the illustrated embodiment, the fluorescence scanner system 40 comprises a processor 245 that is communicatively coupled with a data storage area 45 that can include, e.g., volatile and persistent computer readable storage mediums. The processor 245 executes programmed modules in data storage 245 to control the macro camera 240, TDI line scan camera 205, focusing optics 210, motorized filter cube turret 215, and objective positioner 220 that is coupled to the objective lens 225. The processor also executes programmed modules in data storage 245 to control the illumination module 235, motion controller 250 and motorized stage 255 that supports the sample 230. The processor also executes programmed modules in data storage 245 to control the light source 265, the optimized epifluorescence illumination module 290 that comprises the epifluorescence illumination optics 270 and the optional beam shaping optics 275, and the motorized excitation filter wheel 280.

In operation, the various components of the fluorescence scanner system 40 and the programmed modules stored in data storage 245 enable automatic scanning and digitizing of the fluorescence sample 230. Microscope slides (not shown) are often used as a platform to support the fluorescence sample 230 and can be securely placed on the motorized stage 255 of the fluorescence scanner system 40 for scanning the sample 230. Under control of the processor 245, the motorized stage 255 accelerates the sample 230 to a substantially constant velocity for sensing by the TDI line scan camera 205, where the speed of the stage is synchronized with the line rate of the TDI line scan camera 205. After scanning of a stripe of image data, the motorized stage 255 decelerates and brings the sample 230 to a substantially complete stop before additional scanning of the same stripe or a different stripe.

The sample 230 can be any type of specimen that has been labeled with florescence dyes or fluorochrome, for example, tissue, cells, DNA and protein are types of samples, just to name a few. The fluorescence sample 230 can also be an array of specimen, for example, tissue sections, DNA, or DNA related material deposited on a substrate. As will be understood by those skilled in the art, any fluorescence specimen that can be interrogated by a fluorescence optical microscope can also be scanned by the fluorescence scanner system 40 to create a digital slide image of the fluorescence sample 230.

Fluorescence molecules are photon sensitive molecules that can absorb light at a specific wavelength (excitation). These photon sensitive molecules also emit light at a higher wavelength (emission). Because the efficiency of this photoluminescence phenomenon is very low, the amount of emitted light is often very low. The low amount of emitted light frustrates conventional techniques for scanning and digitizing the sample 230. Advantageously, use of the TDI line scan camera 205 that includes multiple linear sensor arrays increases the sensitivity of the camera by exposing the same area of the sample 230 to the multiple linear sensor arrays of the TDI line scan camera 205. This is particularly useful when scanning faint fluorescence samples with low emitted light. In alternative embodiments, the TDI line scan camera 205 may include 64, 96 or 120 linear sensor arrays, which may be charge coupled device ("CCD") arrays.

In one embodiment, the TDI line scan camera 205 is a monochrome TDI line scan camera, although the systems and methods described herein are not limited to monochrome cameras. Advantageously, monochrome images are ideal in fluorescence microscopy because they provide a more accurate representation of the actual signals from the various channels present on the sample. As will be understood by those skilled in the art, a fluorescence sample 230 can be labeled with multiple florescence dyes that emit light at different wavelengths, which are also referred to as "channels."

Furthermore, because the low and high end signal levels of various fluorescence samples present a wide spectrum of wavelengths for the TDI line scan camera 205 to sense, it is desirable for the low and high end signal levels that the TDI line scan camera 205 can sense to be similarly wide. Accordingly, in one embodiment a TDI line scan camera 205 used in the fluorescence scanning system 40 is a monochrome 10 bit 64 stage TDI line scan camera. It should be noted that a variety of bit depths for the TDI line scan camera 205 can be employed for use with the fluorescence scanning system 40.

In one embodiment, the fluorescence scanning system 40 uses a high precision and tightly coordinated XY grid to aid in the location of the sample 230 on the motorized stage 255. In one embodiment, the motorized stage 255 is a linear motor based XY stage with high precision encoders employed on both the X and the Y axis. For example, a 50 nanometer encoder can be used on the axis in the scanning direction and a 5 nanometer encoder can be used on the axis that is in the direction perpendicular to the scanning direction and on the same plane. Objective lens 225 is also mounted on the objective positioner 220 which employs a linear motor on the optical axis with a 50 nanometer encoder. In one embodiment, the three XYZ axes are coordinated and controlled in a closed loop manner using motion controller 250 that includes a motion control drive (not shown) and a motion control board (not shown). Control and coordination is maintained by processor 245, that employs data storage area 45 for storing information and instructions, including the computer executable programmed steps for scanning system 40 operation.

In one embodiment, the objective lens 225 is a plan APO infinity corrected objective that is suitable for fluorescence microscopy (e.g., an Olympus 20×, 0.75 NA). Advantageously, objective lens 225 is capable of correcting for chromatic and spherical aberrations. Because objective lens 225 is infinity corrected, other optical components such as filters, magnification changer lenses, etc. can be placed in the optical path above the objective lens 225 where the light beam passing through the objective lens becomes a collimated light beam. The objective lens 255 combined with focusing optics 210 provides the total magnification for the fluorescence scanning system 40 and also provides for focusing on the surface of TDI line scan camera 205. The focusing optics 210 contain a tube lens and an optional 2× magnification changer. In one embodiment, the 2× magnification changer can allow objective lens 255 that is natively 20× to scan a sample 230 at 40× magnification.

For the scanning system 40 to effectively perform fluorescence microscopy, a suitable light source 265 needs to be employed. In alternative embodiments, arc lamps such as mercury, metal halide, xenon lamps or LED light sources can be used for this purpose. In one embodiment, light source 265 is an arc based light source such as a 200 watt mercury based DC operated and processor controlled light source. Advantageously, the light source 265 allows the processor 245 to manage shutter control and iris control. In one embodiment, a liquid light guide (not shown) can be used to deliver light to the field of view of the objective lens 225, where scanning takes place, or to other desirable locations within the fluorescence scanning system 40. For example, a 3 mm core liquid light guide can be used to deliver light.

The fluorescence scanning system 40 additionally includes illumination optics that include epifluorescence illumination optics 270 and optional beam shaping optics 275 that collectively are shown as optimized epifluorescence illumination 290. The epifluorescence illumination optics 270 condenses the excitation light on the sample 230 through the objective lens 225. As is the case in epifluorescence illumination, the emitted light from the sample is also collected with the same objective lens 225. One particular advantage of using epifluorescence illumination is to maximize the blockage of excitation light reaching the multiple linear array sensors of the TDI line scan camera 205. In turn, this also maximizes the amount of emitted light that reaches the multiple linear array sensors of the TDI line scan camera 205.

The epifluorescence illumination optics 270 can be implemented using Dichroic mirrors that provide wavelength dependent reflectivity and transmission. As a result, the excitation light gets reflected off the surface of a Dichroic mirror and is guided through the objective lens 225 to reach the sample 230. However, the emitted light from the sample 230, which is at a higher wavelength, will pass through the Dichroic mirror and reach the multiple linear array sensors of the TDI line scan camera 205.

The epifluorescence illumination optics 270 also collimates the light from the light source 265. In alternative embodiments, this is accomplished using Kohler or Critical illumination. Kohler illumination provides the most uniform light illumination on the sample 230 to minimize shading in digital slide images while Critical illumination provides the maximum light intensity on the sample to decrease the necessary imaging exposure time. Both Kohler and Critical illumination can be employed by the fluorescence scanning system 40.

In one embodiment, the epifluorescence illumination optics 270 include relay lens tube optics (not shown) that are designed to collimate the light received from light source 265 through a liquid light guide (not shown) and deliver the light to the sample 230. In this embodiment, the light profile on the sample has minimal roll off within the imaging view through the objective lens 225.

In an alternative embodiment, the optional beam shaping optics 275 operate to illuminate just the portion of the sample 235 that is being sensed by the multiple linear array sensors of the TDI line scan camera 205. Advantageously, the beam shaping optics 275 reshape the illumination area from its natural circular shape into a thin oval shape that closely approximates the rectangular sensor area. The reshaped illumination area advantageously also receives increased light energy. Reshaping the illumination area is a vast improvement over conventional masking, which discards all of the light energy outside of the rectangular mask. Advantages of the optional beam shaping optics 275 include: (a) preserving the sample from redundant exposure to the excitation light and thereby minimizing photobleaching of the sample; and (b) increasing the light energy delivered to the illumination area on the sample and thereby allowing shorter exposure times (i.e., higher line rates) during scanning of the sample 230 to create a digital slide image. In combination, these two can provide a significant advantage.

The fluorescence scanning system 40 also includes motorized excitation filter wheel 280 that facilitates configuration and use of various filters. It is desirable to have certain filters available to increase the effectiveness of fluorescence microscopy. Some of the desirable filters include: (a) an excitation filter that narrows down the broad band light generated from the light source 265 to the specific band needed for excitation of the sample 230; (b) an emission filter to filter out excess light and possibly excitation light that may reach one or more of the linear array sensors of the TDI line scan camera 205; (c) a Dichroic mirror as described above for use with epi-fluorescence illumination. Other filters can also be included.

In one embodiment, the fluorescence scanning system 40 includes a motorized wheel for excitation filters, a motorized wheel for emission filters and a motorized wheel for Dichroic mirrors. Sliders can also be used in place of wheels. In an alternative embodiment, the fluorescence scanning system 40 includes a motorized excitation filter wheel 280 and a motorized filter cube turret 215 that includes the emission filter and the Dichroic mirrors. One particular advantage of separating the excitation filter(s) from the emission filter(s) and the dichroic mirrors is related to the use of a TDI line scan camera 205 that is monochrome. Specifically, use of a monochrome TDI line scan camera 205 causes each stripe region of the sample 230 to be scanned and digitized multiple times—once for each emission wavelength (i.e., channel) to be interrogated. Registration of the multiple scans of a single stripe is therefore critically important to allow integration of the multiple scans into a single image that includes information from each channel.

Additionally, because the motorized filter cube turret 215 includes an emission filter and the Dichroic mirrors, the motorized filter cube turret 215 can implement a filter configuration in which multiple band filter cubes (Dichroic mirrors and emission filters) and single band excitation filters are used in combination (called a "Pinkel" configuration). Use of the Pinkel configuration advantageously allows scanning and digitization of the sample 230 multiple times while changing only the excitation filter using the motorized excitation filter wheel 280. Consequently, no mechanical or optical registration issues will be observed between images of the same stripe on the sample because there is no moving component in the imaging path. This is a significant advantage of separating the excitation filter(s) from the emission filter(s) and Dichroic mirrors when using a line scan camera (such as TDI line scan camera 205) that scans the same area of the sample 230 multiple times and combines the resulting multiple images.

In one embodiment, motorized excitation filter wheel 280 is a six position wheel that can accommodate standard 25 mm filters. The motorized excitation filter wheel 280 is under the control of the processor 245. As will be understood by those skilled in the art, any standard fluorescence filter can be used. Preferably, hard coated filters are used with the scanning system 40 because they are more durable and are easy to clean.

In one embodiment, motorized filter cube turret 215 is also a six positioned turret that holds filter cubes, for example standard Olympus filter cubes can be used. The motorized filter cube turret 215 is under the control of the processor 245. Both the motorized excitation filter wheel 280 and the motorized filter cube turret 215 filter are automatically placed in the illumination path or imaging path under control of the processor 245 depending on the particular fluorochromes on the sample 230 and the available filters configured in the fluorescence scanning system 40.

One particular challenge when imaging fluorescence samples is recognizing the sample 230 on the microscope slide and determining the area to be scanned and digitized into a digital slide image. Moreover, fluorescence samples often times appear to be transparent, which amplifies this challenge because regular imaging of the fluorescence sample using regular lighting does not necessarily provide a means to recognize the specimen on the slide. Accordingly, illumination module 235 is configured to apply oblique illumination to the fluorescence sample 230. Macro camera 240 is configured to capture the image of the sample after it is illuminated with oblique lighting by the illumination module 235. Advantageously, the tissue in the resulting image has enough contrast to be recognizable.

In one embodiment, illumination module 235 uses a white LED module (not shown) integrated with a beam diffuser lens (also not shown) positioned at an angle to illuminate the sample 230 at an appropriate angle. In one embodiment, oblique illumination at an angle of 30 degrees is used (as measured with respect to the surface of the microscope slide). However, it should be understood that oblique illumination at any angle in the range of 0 degrees to 85 degrees can be used. A zero degree angle (e.g., illuminating the sample 230 through the thickness of the slide) can be accomplished using, for example, a linear fiber. In one embodiment, additional shrouding around the illumination module 235 is provided to better channel the oblique light hitting the surface of the sample 230. Shrouding around the macro camera 240 is also provided to increase the amount of reflected light off the sample 230 that is captured by the macro camera 240 while also minimizing the amount of illumination light that is captured by the macro camera 240.

The processor 245 may include one or more processor cores, as will be understood by those skilled in the art. Additional separate processors may also be provided to control particular components or perform particular functions. For example, additional processors may include an auxiliary processor to manage data input, an auxiliary processor to perform floating point mathematical operations, a special-purpose processor having an architecture suitable for fast execution of signal processing algorithms (e.g., digital signal processor), a slave processor subordinate to the main processor (e.g., back-end processor), an additional processor for controlling the TDI line scan camera 205, the stage 255, the objective lens 225 or a display (not shown). Such additional processors may be separate discrete processors or may be integrated with the processor 245.

The processor 245 is preferably electrically connected to the various components of the fluorescence scanning system 40 in order to provide control and coordination and overall management of the fluorescence scanning system 40. Alternatively, the processor 245 can be in wireless communication with one or more of the various components of the fluorescence scanning system 40.

The data storage area 45 provides storage of data and instructions for programs executing on the processor 245. The data storage area 45 preferably includes volatile and persistent storage of the data and instructions and may include a random access memory, a read only memory, a hard disk drive, removable storage drive, and the like.

The scanning system 40 may also include a communication interface (not shown) that allows software and data to be transferred between the scanning system 40 and external devices that are directly connected (e.g., a printer) or external devices such as the operator station 20, user station 30, and the image server system 50 that are connected via the network 60.

In one embodiment, computer executable instructions (e.g., programmed modules and software) are stored in the data storage area 245 and when executed, enable the scanning system 40 to perform the various functions described herein. In this description, the term "computer readable storage medium" is used to refer to any media used to store and provide computer executable instructions to the scanning system 40 for execution by the processor 245. Examples of these media include data storage area 245 and any removable or external storage medium (not shown) communicatively coupled with the scanning system 40 either directly or indirectly, for example via the network 60.

Figure 3:
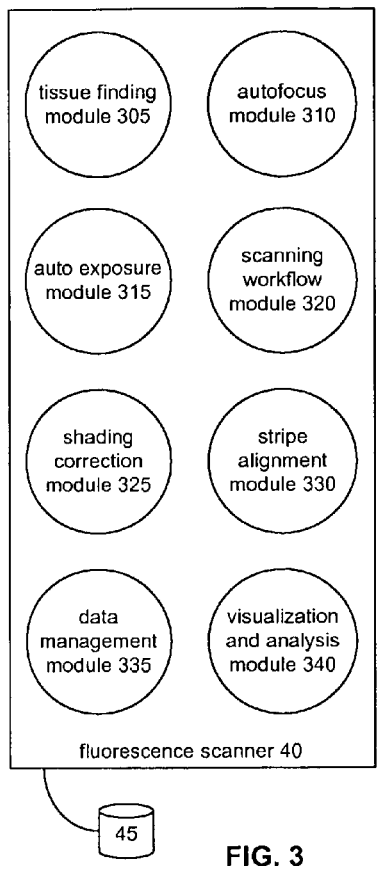
FIG. 3 is a block diagram illustrating an example set of modules in the fluorescence scanner system 40 according to an embodiment of the invention.

FIG. 3 is a block diagram illustrating an example set of modules in the fluorescence scanner system 40 according to an embodiment of the invention. In the illustrated embodiment, the modules include the tissue finding module 305, autofocus module 310, auto exposure module 315, scanning workflow module 320, shading correction module 325, stripe alignment module 330, data management module 335 and the visualization and analysis module 340. In certain combinations, the various illustrated modules collaborate to perform whole slide fluorescence scanning. Certain methods that are performed by the various modules are later described with respect to FIGS. 4-8.

The tissue finding module 305 operates to determine the location of the sample 230 on the microscope slide. The location of the sample is determined with respect to the previously described XY coordinates for the motorized stage. The tissue finding module 305 analyzes image data from the macro camera 240 to determine the location of the tissue. Advantageously, oblique illumination of the sample 230 results in the macro camera 240 providing a high contrast image of the sample 230 to the tissue finding module 305. The tissue finding module 305 analyzes the high contrast image from the macro camera 240 to determine the location of the sample 230. For example, the highest contrast areas may define the perimeter of the specimen to allow the tissue finding algorithm 305 to determine an outline of the sample 230. In one embodiment, the tissue finding module 305 employs a thresholding algorithm which, given an image largely composed of black pixels (representing areas where there is no tissue present) and white pixels (representing areas where there is tissue present), calculates the minimum pixel intensity of a white pixel (the "threshold"). The threshold is then used to classify each pixel in the macro image as being tissue or not tissue. This chosen threshold minimizes the result of the following equation: $\omega_{nt}\sigma_{nt}+\omega_t\sigma_t$ where $\omega_{nt}$ is the probability that a pixel will be classified as not tissue, and $\sigma_{nt}$ is the variance of intensities of pixels classified as not tissue, and $\omega_t$ is the probability that a pixel will be classified as tissue, and $\sigma_t$ is the variance of intensities of pixels classified as tissue.

The autofocus module 310 operates to generate a focus map of the surface of the sample 230 so that the digital slide image that is created as a result of scanning the sample has optimal focus. The autofocus module 310 initially determines a set of points on the sample using the XY coordinates. Next, each point is visited by the TDI line scan camera and the optimal focus height for the objective lens at each point is determined. In one embodiment, the optimal focus height for an XY point can be determined by scanning the XY point on the sample from the top end of the Z range of the objective to the bottom end of the Z range of the objective and then scanning the same point on the sample from the bottom end of the Z range of the objective to the top end of the Z range of the objective and then averaging the two. The height of the objective that provides the highest contrast in the scanned image data is then determined for both scans (i.e., top down and bottom up) and an average height is then calculated as the optimal focus height for that XY point.

In an alternative embodiment, the optimal focus height for an XY point can be determined by scanning the point on the sample from the top end of the Z range of the objective to the bottom end of the Z range of the objective, or vice versa. The height of the objective that provides the highest contrast in the scanned image data is then determined to be the optimal focus height for that XY point. This technique is less desirable.

The result of either technique for determining the optimal focus height for an XY point is a set of focus points that each comprise an XY location and a focus height. The set of focus points is then used to calculate a non-planar focal surface that covers the scan area. The scan area can include the entire sample 230 or just a portion of the sample 230.

One particularly challenging aspect of determining the optimal focus height for an XY point on the sample 230 arises from the use of the TDI line scan camera 205. This is because the sensor in a TDI line scan camera comprises a plurality of linear sensing arrays (e.g., 64 or 96) located side by side in a uniformly spaced, parallel manner. During relative motion scanning, as the sample 230 moves perpendicular to the linear sensing arrays, the sample 230 is sensed by the first array, then the second array, and so on. Advantageously, this provides multiple exposures of each area of the sample 230 as it moves relative to the sensor. The multiple exposures are then combined to create the resulting image, which benefits from the increased exposure time without sacrificing the scanning speed. The increased exposure time is particularly useful when used for faint fluorescence samples, as explained above.

However, this advantage of the TDI line scan camera 205 becomes a liability when the perpendicular relative motion of the sample and the linear sensing arrays is removed, as is the case when determining the optimal focus height for an XY point on a sample. For example, as the TDI line scan camera 205 travels from the top end of its Z range to the bottom end, each of the multiple linear sensing arrays captures image data for the portion of the sample 230 it can "see." As the TDI camera 205 successively integrates the image data from the various linear sensing arrays, the image data is not from the same exact portion of the sample 230. Accordingly, when the image data from the various linear sensing arrays are combined to create a resulting image, the resulting image appears blurred. This is referred to as spatial blurring.

A related problem with using the TDI line scan camera 205 is referred to as temporal blurring. In temporal blurring, the problem is that as the objective travels through its Z range, the first linear array sensor captures its image data at time t1. This image data is then integrated with the image data captured by the second linear array sensor at time t2, and so on. By the time the $96^{th}$ linear array sensor is capturing its image at t96, the Z level of the objective has changed sufficiently to be on a different focal plane. Thus, temporal blurring is also a challenge for identifying the optimal focus height for an XY point on the sample 230.

Accordingly, the autofocus module 310 operates such that for each XY focus point, the objective lens travels from the top end of its Z range to the bottom end of its Z range and then additionally travels back from the bottom end of its Z range to the top end of its Z range. The result of the top-to-bottom scan and the bottom-to-top scan are then averaged to determine the optimal focus height. This effectively eliminates the temporal blurring problems associated with using the TDI line scan camera 205 for identifying the optimal focus height at a focus point and allows the autofocus module 310 to use the average height of the objective that provides the most contrast in the top-to-bottom scanned image data and the bottom-to-top scanned image data as the optimal focus height for each XY point.

In an alternative embodiment, to eliminate problems associated with temporal blurring, during the top-to-bottom scan and during the bottom-to-top scan, the image data from each of the linear sensing arrays (e.g., from all 96 arrays) that is captured at each Z position is integrated into a single line of data. In this fashion, there would still be spatial blurring, but the temporal blurring is eliminated.

The autoexposure module 315 operates to determine the optimum exposure time for each of the fluorochromes on a sample being scanned by the fluorescence scanning system 40. The exposure time determination process typically uses a small area of the sample 230 that is representative of the overall sample 230 and the particular fluorochrome (i.e., the particular channel). The autoexposure module 315 obtains focused image data from a small area of the sample 230 and analyzes the image data to calculate an estimated optimal exposure time for the small area of the sample 230. The scan and analyze and calculate process is then repeated until the actual exposure time used by the TDI line scan camera 205 is substantially equal to the estimated optimal exposure time that is calculated.

Once the optimal exposure time has been calculated for one fluorochrome (i.e., channel) the autoexposure module 315 stores that exposure time in a data storage area for later use during the scan. The autoexposure module 315 then proceeds to determine the optimal exposure time for any remaining fluorochromes on the sample 230. Advantageously, the scanning system 40 employs a monochrome TDI line scan camera 205 and separate excitation and emission filter wheels, which allows the exposure time for each fluorochrome to be calculated independent of the other fluorochromes. This arrangement of the fluorescence scanning system 40 provides a significant advantage over fluorescence scanning systems that attempt to capture image data from multiple fluorochromes during one scanning movement.

The scanning workflow module 320 operates to manage the overall process for creating a digital slide image of a fluorescence sample 230 using the fluorescence scanning system 40. As previously described, the scanning system 40 uses a monochrome TDI line scan camera 205 with high sensitivity and high bit depth to achieve optimum imaging performance. However, fluorescence samples 230 are typically marked with multiple fluorochromes, which causes light to be emitted from the sample 230 in multiple wavelengths (i.e., channels). Accordingly, when scanning a multi-channel fluorescence sample 230, channel separation is achieved by the fluorescence scanning system 40 by the use of specialized filters. For maximum flexibility, the excitation filter is mounted separately from the emission filter, as described above. This allows for multiple filter combinations by means of a filter wheel having one or more excitation filters combined with a filter cube turret having one or more emission filter cubes. Since the filter wheel is a motor controlled device, to minimize scanning time it is preferable to also minimize filter wheel rotations.

The scanning workflow module 320 implements a very efficient process that advantageously minimizes the number of filter wheel rotations. For example, compared to a conventional image tiling system, the scanning workflow module 320 reduces the number of filter wheel rotations by a factor of 60 to 120. In a conventional image tiling system, for every small image tile, the filter wheel must be positioned "N" times, where N equals the number of channels. For a typical exposure time of 10 milliseconds per tile, significantly more time is spent rotating the filter wheel N times than is spent actually sensing the images. The fluorescence scanning system 40, in contrast, rotates the filter wheel only N times for each scanned stripe. Since a typical scanned image tile is roughly 1 megapixel, whereas a typical scanned stripe is roughly 60 megapixels, for each channel beyond the first, there is a 60 to 1 decrease in the number of filter wheel rotations due to the efficiency of the process implemented by the scanning workflow module 320.

The shading correction module 325 operates to correct for non-uniformity in the epifluorescence illumination optics and the TDI line scan camera 205. The shading correction module 325 scans a small area of the sample 320 (e.g., 1 mm) of the slide at a particular XY coordinate where no sample is present. In one embodiment, the scan is performed using predetermined focus parameters that were determined for the sample 320. The scan is performed at the maximum exposure time of the TDI line scan camera 205 in order to capture the light emitted by any residual dye present on the slide (background fluorescence). The average intensity for each pixel column in the scan is calculated and checked to ensure that an accurate illumination profile can be calculated, and then the shading correction module 325 calculates an illumination correction profile by comparing the average intensity of each pixel column to the maximum average intensity present in the image. This profile is calculated for each fluorochrome (i.e., channel) to be scanned by the fluorescence scanning system 40.

The stripe alignment module 330 operates to align adjacent stripes of image data that are captured by the TDI line scan camera 205. In one embodiment, the high precision XY accuracy of the motorized stage 255 allows each stripe of image data to be abutted against its adjacent neighbor in the resulting single file digital slide image. The high precision XY accuracy of the stage 255 therefore provides sufficiently aligned adjacent stripes without the need for any software implemented alignment that is dependent upon an analysis of the content of the image data. This solves a particular problem with respect to software based alignment of stripes of image data for fluorescence samples 230 that arises because fluorescence sample image data typically does not contain enough contrast in the overlap area of adjacent stripes to allow software based alignment of stripes of fluorescence sample image data.

In an alternative embodiment, the scanning system 40 uses software based alignment of stripes when there is sufficient contrast in the fluorescence sample image data. In this embodiment, the alignment of adjacent stripes is not determined based on a certain number of pixels determined to have the highest contrast in the overlap area of adjacent stripes. Instead, the stripe alignment module 330 calculates a contrast distribution of the entire overlap area of the adjacent stripes. The stripe alignment module 330 then identifies a contrast peak in the contrast distribution of the overlap area and defines a band around the contrast peak. The optimal stripe alignment is determined based on the pixels corresponding to the band around the contrast peak. Advantageously, oversaturated pixels are ignored when calculating the contrast distribution.

Additionally, for multi-channel fluorescence samples 230, optimal stripe alignment between adjacent stripes can be calculated for each channel and the channel providing the most robust alignment can be used. Advantageously, because the image data from the stripes corresponding to the various channels are combined in the digital slide image, alignment of only one channel between adjacent stripes is needed. Furthermore, the stripe alignment module 330 calculates stripe alignment in the direction perpendicular to the scanning direction one time. This can be calculated based on the high precision XY accuracy of the stage 255 in combination with the beginning of image data capture, which should be the same for all the channels.

The data management module 335 operates to manage the multi-channel image data generated by the TDI line scan camera 205 and related image data and metadata information. Initially, as with brightfield digital slide images, a fluorescence digital slide image scan can be stored in a single digital slide image file. If the sample 230 was scanned at multiple Z levels, the image for each of the various Z levels is also incorporated into the digital slide image file.

Additionally, because fluorescence scans typically include image data from multiple channels and each channel is related to the same sample 230, it is advantageous to store the multi-channel image data a single digital slide image file. Furthermore, it is also valuable to store related sub-imagery data and metadata related to instrument acquisition settings, image data descriptors, and sample information in the digital slide image file. Moreover, any known or scan-time computed inter-image relationships can also be stored in the digital slide image file.

Related sub-imagery may include an image of the slide label (e.g., a barcode), macro images of the whole slide, and a thumbnail of the acquired image. Meta data related to instrument acquisition settings may include exposure time, filter specifications, light source specifications, and calibration information. Meta data related to image data descriptors may include the intensity distribution of the image pixels, automatically determined regions of interest and regions of disinterest, image features such as contrast distribution, frequency distribution, texture as well as figures of merit. Meta data related to sample information may include the tissue type and preparation as well as targeted biologic feature. Inter-image relationships include image translation and image rotation data.

In one embodiment, the fluorescence digital slide image file is structured and stored as a tiled, multi-layer image. The base layer is at the original scan resolution and subsequent layers are sub-sampled resolutions that form an image pyramid. Each layer is made up of one or more tiles and each tile of a layer can be compressed with a lossless or a lossy compression algorithm for improved disk and memory utilization, file transfer speeds and network image serving rates.

For multi-channel digital slide images, the base layer and each subsequent layer comprises the image data for each channel. For example, a four channel digital slide image would have a base layer divided into four quadrants where each quadrant included a complete image of the sample 230 at one of the four quadrants.

The digital slide images are stored in a data storage area, for example the data storage area 45 of the scanning system 40 or the data storage area 55 of the image server system 50. In one embodiment, the data management module 335 itemizes each scanned image with respect to its associated patient, specimen and slide and may also record results of quantitative analysis in association with the stored digital slide image. The data management module 335 may also provide a user with access to all of the stored information as well as provide an interface to hospital and laboratory information systems for data sharing.

In an alternative embodiment, separate digital slide images can be created for each channel at which that the specimen 230 was scanned. In such an embodiment, a secondary file that references the related digital slide image files is created. The secondary file comprises the inter-image relationships as well as visualization preferences and adjustments (described below). This secondary file is called a fused image.

The visualization and analysis module 340 operates to facilitate viewing and analysis of a fluorescence digital slide image file. Each fluorescence digital slide image can be viewed at each of the various separate channels and/or viewed as a fused image where the image data from the various separate channels is overlayed into a single view of the sample that includes two or more channels. When the digital slide image is viewed (in separate or fused channels) the image of the entire sample 230 is available for real time image navigation, rotation, zooming, magnification and Z level depth traversal.

In one embodiment, the multiple fluorochrome channels may be viewed simultaneously by arranging them side by side or in a grid formation. Advantageously, the images are registered to enable synchronous navigation. For example, a four channel scan may be arranged in a four quadrant layout. In one embodiment, zooming one image causes all four quadrants to similarly zoom. Additionally, panning left on one quadrant, for example, pans left on all four quadrants, and so on.

Image viewing adjustments such as brightness, contrast, gamma and false coloring are automatically determined using the stored image descriptors and the acquisition settings. In one embodiment, viewing adjustments can be made by a user at the user station 30 for the individual images and/or for a fused image (i.e., the combined image of two or more individual channel images). In addition, when viewing a fused image the relative translation and rotation corrections may be adjusted.

Interactive image exploration tools are also enabled by the digital visualization and analysis module 340 to instantly access fluorochrome responses on a cellular basis. Additionally, predetermined regions of interest may contain annotation that can be displayed to a user at the user station 30 to indicate meaningful biologic responses or to automatically quantitatively analyze. Additionally, the visualization and analysis module 340 may provide a user at the user station 30 with tools to annotate regions of interest and then store such annotations in the digital slide image file in relation to the base layer image. Advantageously, such annotations can be a useful to guide to document artifacts in an image, regions of interest in an image, or to identify a region of an image for reporting or quantitative analysis.

Additionally, the visualization and analysis module 340 may use predetermined or otherwise identified image features to locate similar image data or patterns using content based image retrieval techniques. Advantageously, this utility can provide a user at the user station 30 with related case information and image data.

In one embodiment, a client-server architecture permits a user at the user station 30 to view a fluorescence digital slide image located at the image server system 50 or the scanning system 40 by requesting the compressed image tiles at a specified pyramid level on an as needed basis and by performing client side caching of tiles in anticipation of user requests.

The digital visualization and analysis module 340 additionally operates to facilitate whole slide quantitative analysis of the fluorescence digital slide images, whether the image is a quadrant style image or a fused style image. In one embodiment, the digital visualization and analysis module 340 can facilitate a quantitative analysis of a particular region of interest instead of the entire digital slide image. Analysis results can be stored in a data storage area such as data storage areas 45, 55, 25 or 35 for use with data management and reporting.

Figure 4:
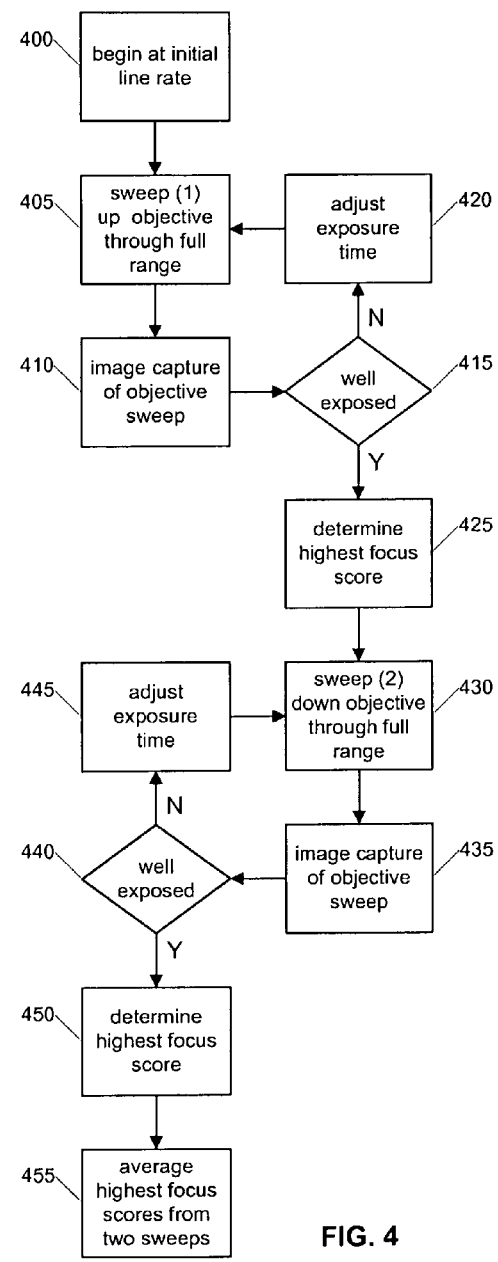
FIG. 4 is a flow diagram illustrating an example process for macro focus in a fluorescence scanner system according to an embodiment of the invention.

FIG. 4 is a flow diagram illustrating an example process for macro focus in a fluorescence scanner system according to an embodiment of the invention. The illustrated processes can be implemented by the fluorescence scanning system 40 previously described with respect to FIGS. 1-3. Notably, in contrast to fluorescence digital slide image creation, in brightfield digital slide image creation the line scan camera operates at a single fixed exposure time. However, because the fluorescence scanning system 40 works by sensing light emitted from the sample instead of light blocked by the sample (as in brightfield), and because the amount of light emitted can vary by several orders of magnitude from one slide from the next, it is not possible to use a single fixed exposure time for focusing all slides in fluorescence digital slide image creation. Additionally, it is not possible to always use a pre-stored exposure time or one calculated using an automatic exposure adjustment algorithm, as the automatic exposure adjustment algorithm would require that the sample be in focus before it could give accurate results. As a result, in fluorescence digital slide image creation the optimal exposure time is advantageously determined while a macro focus is being performed.

Accordingly, when a macro focus is initiated, the TDI line scan camera 205 is initialized with an initial fixed exposure time, as shown in step 400. Next, in step 405 the objective lens 225 is swept from one end of its range to the other end of its range (e.g., the bottom to the top). As shown in step 410, the image data from this objective sweep is captured into a data storage area (e.g., an image buffer) and then in step 415 it is determined if the image data is well exposed.

For example, while the objective sweeps upward, the TDI line scan camera 205 captures data at the initial line rate (i.e., a constant exposure time) and the resulting lines of image data are stored in a data storage area (e.g., a two dimensional image buffer). Each line of image data in the two dimensional image buffer is a single row of pixels with the objective at a different distance away from the sample. Since the TDI line scan camera 205 captures lines at a constant exposure time, the velocity of the objective lens 225 during the sweep determines the amount of distance between successive lines. Accordingly, the top line of the image buffer is an image of the sample 230 as it is seen when the objective is at the minimum distance from the sample 230, and the bottom line of the image buffer is an image of the sample 230 as it is seen when the objective is at the maximum distance from the sample 230.

After the image data from the first sweep is captured in step 410, the image data is passed through an exposure adjustment algorithm in step 415 to determine if the image data is over-saturated or under-saturated (i.e., if it is exposed, meaning that the line rate is appropriate). If the image data is not well-exposed, the exposure time is adjusted in step 420, for example by doubling or halving the line rate. Then the process loops back to step 405 where the objective sweep is preformed again and image data is captured. This process may loop through several iterations until it is determined in step 415 that the image data is well exposed.

Once the image data is determined to be well-exposed in step 415, the image data is processed to determine the highest focus score, as shown in step 425. In one embodiment, each row of pixels in the image buffer is scored and the image data with the highest contrast is determined to have the highest focus score. Accordingly, the optimal focus height for the objective is determined by determining the row of pixels in the image buffer with the highest focus score. In one embodiment, if the highest focus score meets or exceeds a predetermined threshold, the macro focusing process continues on for a second sweep of the objective in the opposite direction of the first sweep.

Advantageously, sweeping the objective in the opposite direction and repeating the focus score process and then averaging the objective lens height of the highest focus score from each objective sweep eliminates the bias introduced by using a TDI line scan camera 205. Accordingly, in step 430 the objective lens 225 is swept from one end of its range to the other end of its range (e.g., the top to the bottom). As shown in step 435, the image data from this objective sweep is captured into a data storage area (e.g., an image buffer) and then in step 440 it is determined if the image data is well exposed. If the image data is not well exposed, then the process loops back through step 445 where the line rate is adjusted and iterates until well exposed image data has been captured, as determined in step 440. Once well focused image data is obtained, the image data is analyzed to determine the highest focus score, as shown in step 450.

When determining the highest focus score for digital slide images created using brightfield digital slide imaging, the focus score can be calculated using the following equation:

$$\frac{\sum_{x=8}^{width} (p_x - p_{x-8})^2}{width}$$

where $p_x$ is the intensity of the pixel at index x. However, when determining the highest focus score for digital slide images created using fluorescence digital slide imaging, that equation results in higher scores for transitional areas of the image where the image just begins to come into focus. This is because the sum of a larger number of small differences between pixel intensities present in the transitional areas outweighs the smaller number of large differences between pixel intensities present in areas of the image where the sample is in best focus. Accordingly, conventional brightfield focus scoring cannot be used on fluorescence digital images.

The digital images created by the fluorescence scanning system 40, however, tend to have higher intensities as they become more in focus. Accordingly, the focus scoring equation used for fluorescence images becomes:

$$\frac{\sum_{x=1}^{width} (p_x \cdot (p_x - p_{x-1}))^2}{width}$$

where $p_x$ is the intensity of the pixel at index x. Advantageously, because the difference in pixel intensity is weighted by the pixel intensity in this equation and because of the correlation between focus and intensity in fluorescence digital images, using this equation for focus scoring of fluorescence digital images causes the higher pixel intensities representing the more in focus image data to have the highest focus scores. Additional operations such as filtering noise from the digital images before scoring may also be employed to improve performance and filter out false-positives, for example false-positives may be generated when attempting to focus on areas where sample is not present.

Once the highest focus score has been determined in step 450, the objective lens height at the highest focus score for the first sweep and the objective lens height at the highest focus score for the second sweep are then averaged to determine the optimal focus height, as shown in step 455.

Advantageously, the exposure adjustments described above with respect to steps (405, 410, 415, 420) and (430, 435, 440, 445) only need to be performed during the macro focus operation. When the fluorescence scanning system 40 focuses on individual XY focus points to determine the topography of the sample 230 and generate a focus map, scanning system 40 uses the exposure rate determined by the macro focus operation.

Figure 5:
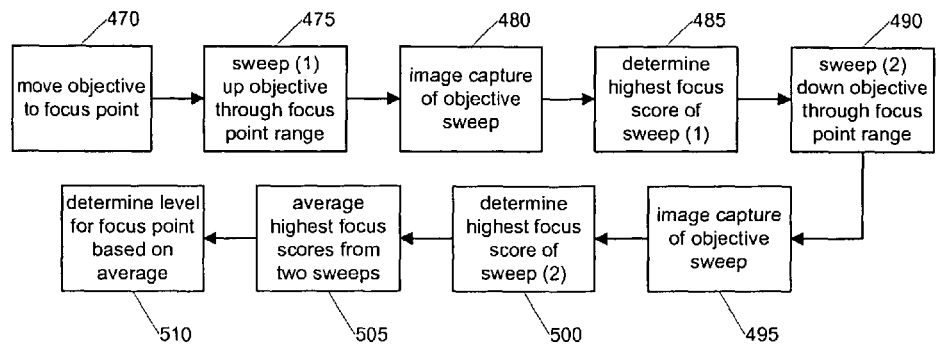
FIG. 5 is a flow diagram illustrating an example process for autofocus in a fluorescence scanner system according to an embodiment of the invention.

FIG. 5 is a flow diagram illustrating an example process for autofocus in a fluorescence scanner system according to an embodiment of the invention. The illustrated processes can be implemented by the fluorescence scanning system 40 previously described with respect to FIGS. 1-3. As explained above, spatial blurring and temporal blurring introduce particular challenges when determining a plurality of focus points on the sample 230 to generate a focus map that can be used later to guide the objective lens when rapidly scanning the fluorescence sample 230.

Initially, a set of XY points on the sample 230 are identified for use in creating the focus map. In step 470 the scanning system 40 moves the objective to a first of the XY focus points. In one embodiment, it is the motorized stage 255 that physically moves in the XY plane to place the first XY focus point under the objective. Next, in step 475 the objective lens sweeps through its full range of motion, for example from its lowest point to its highest point. As the objective moves up from its lowest point to its highest point, image data is captured into a data storage area (e.g., an image buffer) in step 480. When the image data from the full sweep has been captured, it is scored in step 485 to determine the line of image data with the highest focus score. The objective lens height when that particular highest focus score line of data was captured is identified and stored.

Next, in step 490 the objective lens sweeps through its full range of motion in the opposite direction as the first sweep, for example from its highest point to its lowest point. As the objective moves up from its highest point to its lowest point, image data is captured into a data storage area (e.g., an image buffer) in step 495. When the image data from the full sweep has been captured, it is scored in step 500 to determine the line of image data with the highest focus score. The objective lens height when that particular highest focus score line of data was captured is identified and stored. In step 505, the objective lens height for the up sweep highest focus score line of data and the objective lens height for the down sweep highest focus score line of data are averaged. The average height is then determined to be the objective lens height for the XY focus point to be used in creating the focus map.

Figure 6:
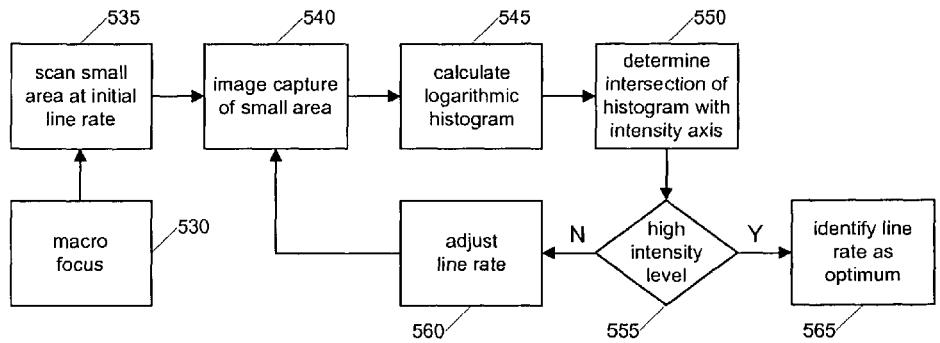
FIG. 6 is a flow diagram illustrating an example process for determining an optimal auto exposure line rate in a fluorescence scanner system according to an embodiment of the invention.

FIG. 6 is a flow diagram illustrating an example process for determining an optimal autoexposure line rate in a fluorescence scanner system according to an embodiment of the invention. The illustrated processes can be implemented by the fluorescence scanning system 40 previously described with respect to FIGS. 1-3. Moreover, determining an optimal exposure time using the illustrated process can also be implemented by a conventional image tiling system that employs an area scan camera. As previously explained, because fluorescence digital slide imaging captures light emitted from the sample 230 and the intensity of the emitted light can vary by orders of magnitude from slide to slide, it is necessary to determine the optimal exposure time for capturing the emitted light during scanning and digitizing the sample 230. Additionally, saturated pixels in fluorescence digital imaging present a particular problem because they are brighter than other pixels and therefore are meaningless in the resulting image data because they do not have any linear correlation with pixels that are not saturated and as a result do not yield accurate data. When creating digital images that will be used for quantitative analysis, it is important to limit the number of pixels in the image that are saturated. Accordingly, when determining the optimal exposure time for a particular sample 230, it is important to limit the number of saturated pixels.

Furthermore, when determining the optimal exposure time for a particular sample 230, it is also important to maximize the dynamic range of the resulting image because underexposed images may not provide sufficient differences in the pixel intensities to be identifiable. Accordingly, determining an optimal autoexposure line rate in a fluorescence scanner system needs to minimize saturation while maximizing pixel intensities.

In the illustrated process in FIG. 6, initially, if the sample 230 has not yet been focused, it is focused as shown in step 530. Focusing the sample may be accomplished by the process previously described with respect to FIG. 4 or FIG. 5 or both. Once the sample 230 is in focus, in step 535 a small region of the sample 230 is identified and scanned at the initial line rate (i.e., exposure time) and the image data from the scan is stored in a data storage area (e.g., an image buffer) as shown in step 540. For example, the small region of the sample 230 may be approximately 1 mm×1 mm and the initial line rate that is used can be determined in the focus process of step 530.

Next, in steps 545 to 560, the optimal exposure time for the scanned image data captured in the image buffer is determined and the line rate is adjusted accordingly. The process of scanning a small region of the sample 230 and determining the optimal exposure time and adjusting the line rate then iterates until the intensity level of the captured pixels is at its highest (with minimal saturation of pixels). The line rate is then identified in step 565 as the optimum line rate for the optimal exposure time when creating a digital slide image of the fluorescence sample 230.

Advantageously, because the intensity of the light emitted by a fluorescence sample 230 approximates a Poisson distribution and because camera sensors that are not at saturation are linear with respect to the amount of light hitting the sensor, the histogram of the image data captured in the image buffer also approximates a Poisson distribution. Furthermore, because a primary objective of determining the optimal line rate (i.e., the optimal exposure) is to limit the number of saturated pixels, only the downward slope of the histogram is considered.

Accordingly, the scanning system 40 treats the distribution of the histogram as an exponential decay function such that each non-zero value in the histogram is scaled by taking the base-2 logarithm, which results in a logarithmically scaled histogram approximating a line segment, as shown in step 545. Next, a linear regression analysis is performed on the scaled histogram to yield a linear trend line with a negative slope and the intersection of the histogram with the intensity axis is determined by locating the x-intercept of the trend line, as shown in step 550. The x-intercept represents the intensity at which the number of pixels with this intensity is zero and is determined by using the slope of the trend line and the y-intercept.

Once the intersection of the histogram and the intensity axis is determined for the scanned image data, it is compared against the optimal value representing a pixel intensity slightly below the saturation point of the TDI line scan camera 205. If the image data is within a predetermined (e.g., user configurable) tolerance of the saturation point of the TDI line scan camera 205, as determined in step 555, the image is considered well-exposed and the current line rate is identified as the optimal exposure time/optimum line rate as shown in step 565. If the image data is not within the predetermined tolerance of the saturation point of the TDI line scan camera 205, the ratio of optimal peak intensity to actual peak intensity is calculated and in step 560 the exposure time (i.e., line rate) of the TDI line scan camera 205 is adjusted using that ratio. The process then iterates until the optimum line rate is identified.

Figure 7:
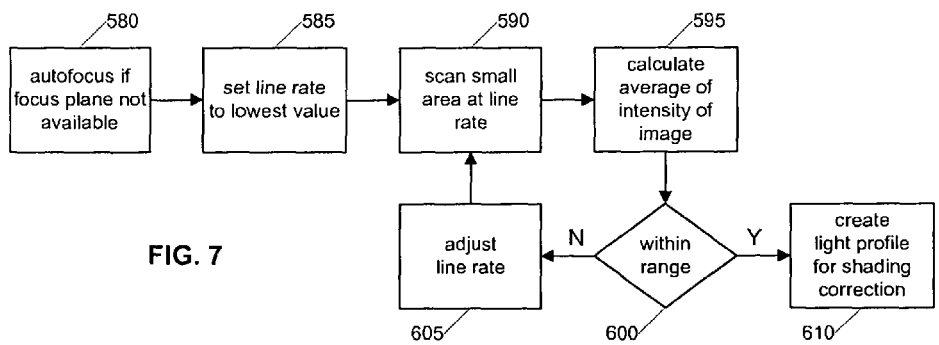
FIG. 7 is a flow diagram illustrating an example process for acquiring images for shading correction according to the present invention.

FIG. 7 is a flow diagram illustrating an example process for acquiring images for shading correction according to the present invention. The illustrated processes can be implemented by the fluorescence scanning system 40 previously described with respect to FIGS. 1-3. Advantageously, shading correction of fluorescence digital slide images compensates for the loss of illumination light (e.g., by roll off) that is necessary to acquire images with minimal shading artifacts on the edges of stripes. Accordingly, it is advantageous to determine an illumination profile for a sample 230 that is to be scanned into a digital slide image. The illumination profile is determined based on the background fluorescence of a slide with a fluorescence sample 230. The illumination light profile can be determined using a clear point under the cover slip of the slide. Preferably, the clear point is in an area of the slide that does not contain any fluorescence labeled sample 230.

Accordingly, the light profile acquired from the background fluorescence can be used to compensate for illumination light roll off.

Initially, in step 580 the image of the sample 230 is brought into focus. This can be accomplished by the previously described macro focus or autofocus process. In one embodiment, in step 580 at least three focus points are identified on the sample 230. Because the illumination profile of the sample 230 varies depending on the height of the objective lens 225 above the sample 230, which is based on the focus.

Next, in step 585 the initial line rate is set at the lowest value and a small region of the sample 230 is scanned in step 590 and the resulting digital image data is stored in a data storage area (e.g., an image buffer). The size of the scan area can vary. Setting the initial line rate for the highest possible exposure time is advantageous because the background material often has a low fluorescence emission. Next, in step 595 the average intensity of the image data is calculated. If the average intensity is not within a predetermined range, as determined in step 600, the line rate is adjusted in step 605 and the process iterates back to re-scan the small region of the sample 230.

In one embodiment, the adjusted line rate is selected based on a linear mapping of the average intensity calculated in step 595 using the previous line rate. Advantageously, the adjusted line rate is between the line rate that yields the minimum acceptable average intensity and the line rate that yields the maximum acceptable average intensity.

If the average intensity is within the predetermined range (e.g., a user configurable range), a light profile for shading correction of the sample 230 is created, as shown in step 610. In one embodiment, when scanning image data in 10 bit mode, an acceptable predetermined average intensity range is 80-600. Advantageously, determining that the average intensity is with the predetermined range rejects saturated images while also including low end images with average pixel intensities that are higher than the noise level of the TDI line scan camera 205.

In one embodiment, the light profile for shading correction that is created in step 610 is used to compensate for illumination light during scanning. For example, pixel correction coefficients can be determined based on the light profile. The light profile is normalized to the brightest pixel value, which normally appears in the middle of the profile, and then a coefficient or pixel multiplier is calculated for all pixels within the field of view of the TDI line scan camera 205. The above described shading correction can advantageously be performed for all channels of the sample 230.

In an alternative embodiment, an outlier rejection algorithm is employed when shading correction creates a specked image. This is useful when it is not possible or very difficult to locate a clear (i.e., fluorochrome free area) on the sample 230. The outlier rejection algorithm advantageously discards artifacts in the shading corrected image by rejecting pixels that exceed the median of the pixel values in each column. In one embodiment, pixels that are 20 counts higher than the median pixel value are rejected.

Figure 8:
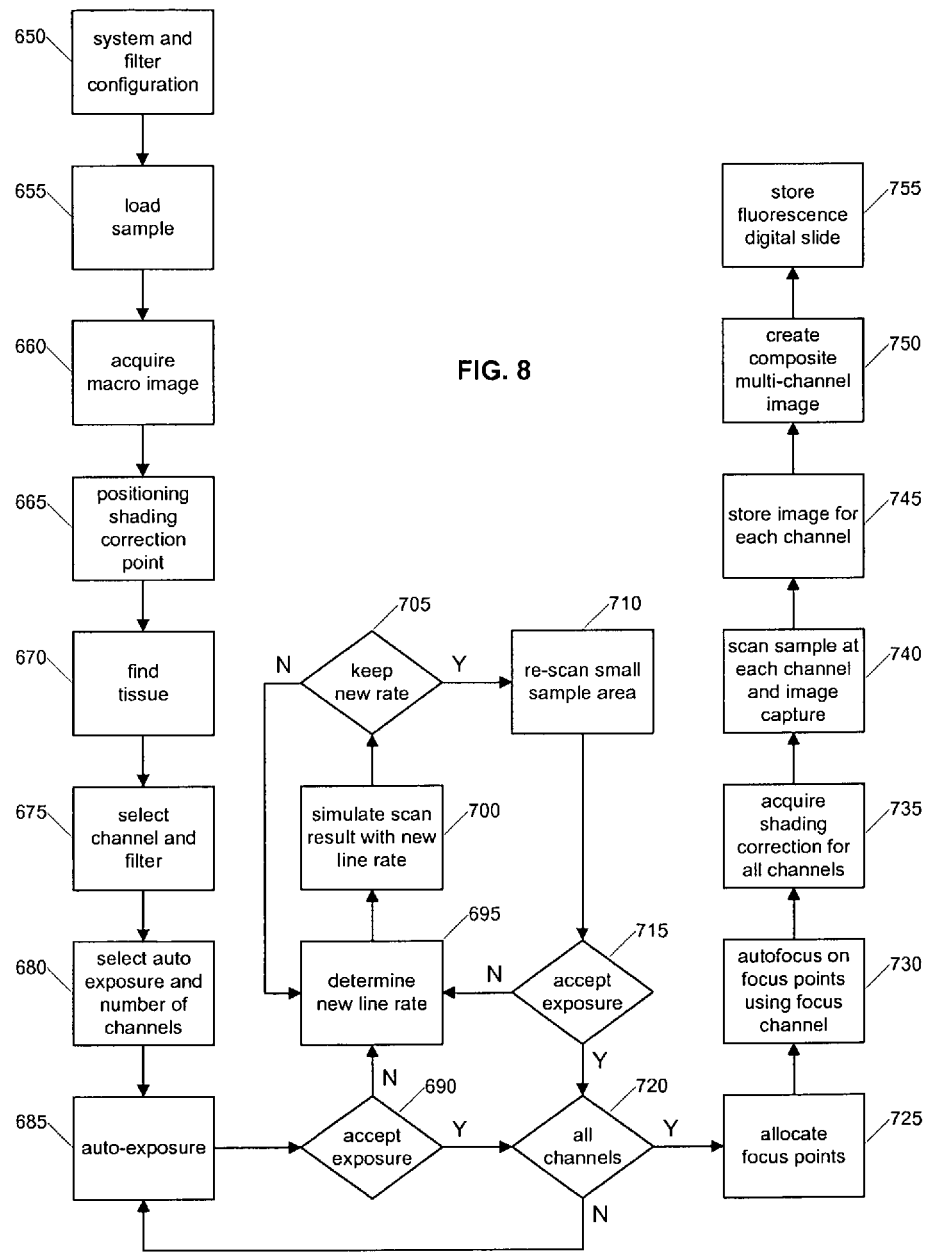
FIG. 8 is a flow diagram illustrating an example scanning workflow process according to the present invention.

FIG. 8 is a flow diagram illustrating an example scanning workflow process according to the present invention. The illustrated processes can be implemented by the fluorescence scanning system 40 previously described with respect to FIGS. 1-3. Initially, in step 650 the scanning system and its excitation filters and emission filters/turrets are configured in accordance with the type of sample 230 being scanned into a digital slide image and the various fluorochromes that the sample 230 might be marked with. In one embodiment, such configuration can be accomplished through a system console or a remote operator station. Additionally, the excitation filters and emission filters/Dichroic mirrors and their relative positions on the filter wheel or turret are identified in step 650.

Next, in step 655 the sample is loaded. This can include placing the microscope slide upon which the sample is disposed into the scanning system 40. After the sample has been loaded, a macro image of the sample is acquired in step 660, for example using the process previously described with respect to FIG. 2. Next, the macro image is analyzed to identify a shading correction point as shown in step 665 and to determine the area(s) on the slide that contain tissue, as illustrated in step 670. Then, in step 675 the various fluorochromes on the sample 230 are identified and correlated to the correct combination of excitation and emission filters to scan the sample 230 at the various channels corresponding to the various fluorochromes.

Because one of the challenges in fluorescence scanning is the identification of the best exposure time for each channel (i.e., each fluorochrome), the scanning workflow automatically identifies the optimum exposure time for each channel, as previously described with respect to FIG. 6. Accordingly, in step 680, the autoexposure process is initiated and the number of channels is determined. In step 685, the autoexposure process is performed. Autoexposure can be automatically performed on all channels or it can be performed on one channel.

In steps 690 and 720, an operator may be engaged to accept the autoexposure results and confirm that all channels have been processed and a valid exposure time determined for each channel. Alternatively, the scanning system 40 may automatically proceed through steps 690 to 720 until an optimal exposure time has been calculated for each channel with no operator input.

Once the autoexposure process is complete and an optimal exposure time for each channel has been determined, in step 725 the scanning system 40 identifies a set of XY focus points on the sample 230. In step 730, the scanning system visits each XY focus point in the set and determines the optimal focus height at each of the XY focus points. The focus points (comprising an XY location and the optimal focus height) are then combined to create a focus map that covers the surface of the sample 230. Then in step 735 the shading correction information is determined for each of the channels.

After the focus map has been created and the shading correction information has been determined, the scanning system 40 begins to scan the sample 230 at each channel, as shown in step 740. The digital image data generated by the scan for each channel is stored in a data storage area in step 745 and then a digital slide image having image data for all of the channels is created in step 750. Finally, the fluorescence digital slide image is stored in a data storage area.

In one embodiment, autofocusing can be interleaved with the scanning process such that the focus points and focus map information are generated for a particular stripe just before that stripe is scanned. Additionally, autofocusing can be done for just a single channel or can be done for each channel.

Because a monochrome TDI line scan camera 205 is employed by the fluorescence scanning system 40, only one channel at a time is scanned. Advantageously, the use of motorized filter wheels allows a single stripe to be scanned multiple times sequentially, once for each channel. In other words, each channel of a single stripe is captured before moving to the next stripe. Because the scanning system 40 uses separate excitation and emission filters, only the excitation filter needs to be rotated to automatically scan the multichannel sample 230 in the preferred Pinkel configuration described above (multi-band filter cube and single band excitation filters). Advantageously, scanning each channel of a single stripe before moving to the next stripe ensures that the resulting image data is optimally registered across all of the channels. Moreover, the number of filter changes is also minimized in comparison to conventional image tiling systems. Alternatively, some or all channels of a sample can be scanned using single band filter cubes having single band excitation/emission filters and Dichroic mirrors. As the scanning process continues, multiple monochrome digital slide images are created that correspond to the number of channels on a sample. These images are stored in a single digital slide image file or alternatively can be stored as separate image files along with an index file that relates the various separate image files. Additionally, a fused image, which is a composite image of all channels with selected false colors can be created.

Various embodiments of the fluorescence scanning system 40 described herein can be implemented using a combination of both hardware modules and software modules. For example, programmed software modules, application specific integrated circuits or field programmable gate arrays can be used interchangeably to implement certain functional modules of the scanning system 40. Accordingly, those skilled in the art will appreciate that the various illustrative modules, blocks, and steps described in connection with all of the figures and the various embodiments disclosed herein can be implemented as hardware, software or a combination of the two. To clearly illustrate this interchangeability of hardware and software, the various illustrative modules, blocks, and steps have been described above in terms of their functionality and whether such functionality is implemented as hardware or software or a combination of the two depends upon the particular application and design constraints imposed on the overall system.

While those skilled in the art can implement the described functionality in varying ways for particular applications under certain design constraints, such implementation decisions should not be interpreted as causing a departure from the scope of the invention. In addition, the grouping of functions within a particular module, block or step or the removal of functions from a particular module, block or step can be accomplished by those skilled in the art without departing from the scope of the invention.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent various embodiments of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

The invention claimed is:

1. A computer implemented method for creating a contiguous digital image of a fluorescence sample, where one or more processors are programmed to perform steps comprising:
   applying oblique illumination to the fluorescence sample;
   capturing a macro image of the fluorescence sample under oblique illumination and storing the macro image in a data storage area;
   analyzing the macro image to identify a region containing at least a portion of the fluorescence sample;
   determining an optimal line rate for use during image capture with a time delay integration (TDI) line scan camera;
   identifying a plurality of focus points on the fluorescence sample, where a focus point comprises an X-Y location and an objective lens height;
   creating a focus map comprising the plurality of focus points;
   after analyzing the macro image to identify the region containing the at least a portion of the fluorescence sample, scanning a digital image of the identified region containing the at least a portion of the fluorescence sample using the TDI line scan camera in accordance with said optimal line rate; and
   combining a plurality of digital image portions into a contiguous digital image of the fluorescence sample.

2. The method of claim 1, wherein scanning a digital image of a portion of the fluorescence sample further comprises:
   scanning the first portion fluorescence sample using a first excitation filter to capture a first channel for the fluorescence sample; and
   scanning the first portion fluorescence sample using a second excitation filter to capture a second channel for the fluorescence sample.

3. A computer implemented method for determining a plurality of focus points for use in creating a contiguous digital image of a microscope sample with time delay integration (TDI) line scan camera, where one or more processors are programmed to perform steps comprising:
   identifying a plurality of focus points on the microscope sample; and,
   for each of the plurality of focus points,
      positioning an objective lens in optical communication with the TDI line scan camera at the focus point;
      scanning a first image of the focus point on the microscope sample with the TDI line scan camera while sweeping the objective lens from a first end of its range in the Z axis to a second end of its range in the Z axis,
      analyzing the first scanned image to identify a portion of the first scanned image having the highest focus score,
      determining a first objective lens height at which the portion of the first scanned image having the highest focus score was captured,
      scanning a second image of the focus point on the microscope sample with the TDI line scan camera while sweeping the objective lens from the second end of its range in the Z axis to the first end of its range in the Z axis,
      analyzing the second scanned image to identify a portion of the second scanned image having the highest focus score,
      determining a second objective lens height at which the portion of the second scanned image having the highest focus score was captured, and
      averaging the first objective lens height and the second objective lens height to determine the optimal objective lens height for the focus point.

4. The method of claim 3, wherein the highest focus score is determined using contrast.

5. The method of claim 3, wherein the highest focus score is determined using pixel intensity.

6. The method of claim 3, wherein the highest focus score is determined using a combination of contrast and pixel intensity.

7. The method of claim 1, wherein analyzing the macro image to identify a region containing at least a portion of the fluorescence sample comprises determining an outline of the fluorescence sample based on contrast in the macro image.

8. The method of claim 7, wherein determining an outline of the fluorescence sample based on contrast in the macro image comprises classifying each pixel in the macro image as either tissue or non-tissue based on an intensity threshold to determine a perimeter of the fluorescence sample.

\* \* \* \* \*